United States Patent [19]
Catani et al.

[11] Patent Number: 5,977,349
[45] Date of Patent: Nov. 2, 1999

[54] CHROMATOGRAPHIC PURIFICATION OF CHLORINATED SUCROSE

[75] Inventors: Steven J. Catani; Duane A. Leinhos; Thomas O'Connor, all of Athens, Ga.

[73] Assignee: McNeil-PPC, Inc., Skillman, N.J.

[21] Appl. No.: 09/022,071

[22] Filed: Feb. 11, 1998

Related U.S. Application Data

[60] Provisional application No. 60/046,980, Feb. 13, 1997.
[51] Int. Cl.⁶ ............................... C07H 1/00; C07G 17/00
[52] U.S. Cl. .......................... 536/124; 536/4.1; 536/115; 536/119; 536/120; 536/122; 536/123.13; 536/127
[58] Field of Search ............................. 536/4.1, 115, 119, 536/120, 122, 124, 123.13, 127

[56] References Cited

U.S. PATENT DOCUMENTS

| | | | |
|---|---|---|---|
| 4,980,463 | 12/1990 | Walkup et al. | 536/124 |
| 5,128,248 | 7/1992 | Dordick et al. | 435/100 |
| 5,498,709 | 3/1996 | Navia et al. | 536/124 |
| 5,530,106 | 6/1996 | Navia et al. | 536/4.1 |

FOREIGN PATENT DOCUMENTS 0 409 549   1/1991   European Pat. Off. .

*Primary Examiner*—James O. Wilson
*Attorney, Agent, or Firm*—Ellen Ciambrone Coletti

[57] ABSTRACT

A process for separating, in the liquid phase, a reaction mixture which comprises a first chlorinated sucrose and at least one additional component selected from the group consisting of at least one other chlorinated sucrose different from said first chlorinated sucrose, salt and solvent, by injecting said reaction mixture onto a fixed bed of solid adsorbent and treating with a desorbent such that:

(a) the first chlorinated sucrose passes through the adsorbent into a first recoverable product stream rich in said first chlorinated sucrose at a rate, which is different than the rate at which, (b) at least one of said additional components passes through the adsorbent into at least a second recoverable stream rich in said additional component.

17 Claims, 9 Drawing Sheets

ILLUSTRATIVE GENERIC SEPARATION OF A MIXTURE VIA ADSORPTION

CHROMATOGRAM WITH SODIUM SULFONIC ACID RESIN, 4% DVB, AS ADSORBENT AND WATER AS DESORBENT.

CHROMATOGRAM WITH SODIUM SULFONIC ACID RESIN, 2% DVB, AS ADSORBENT AND WATER AS DESORBENT.

CHROMATOGRAM WITH SODIUM SULFONIC ACID RESIN, 6% DVB, AS ADSORBENT AND WATER AS DESORBENT.

CHROMATOGRAM WITH SILICA-GEL AS ADSORBENT AND ETHYL ACETATE (2% WATER) AS DESORBENT.

CHROMATOGRAM WITH SILICA-GEL AS ADSORBENT AND ETHYL ACETATE (2% WATER) AS DESORBENT.

CHROMATOGRAM WITH SILICA-GEL AS ADSORBENT AND ETHYL ACETATE(5% METHANOL) AS DESORBENT.

CHROMATOGRAM WITH SULFONIC ACID RESIN, 4% DVB, AS ADSORBENT AND WATER AS DESORBENT.

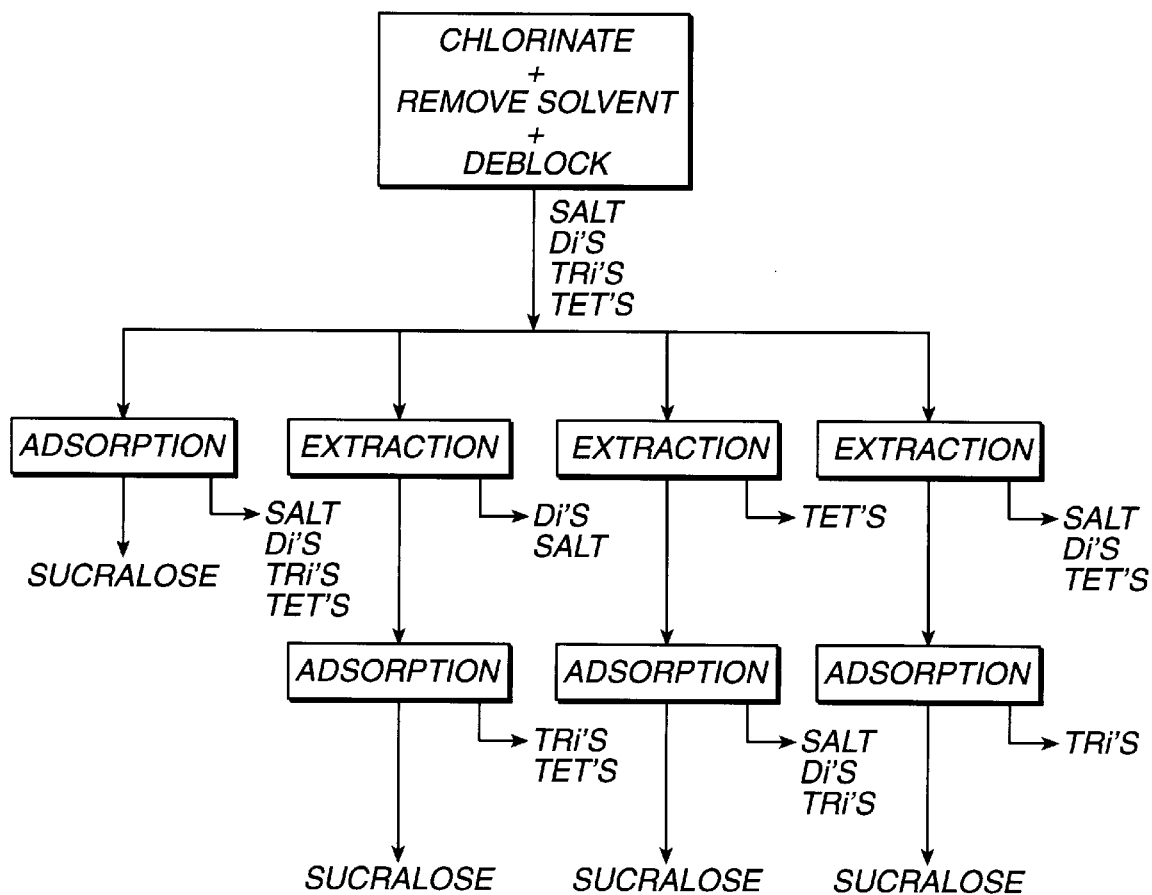

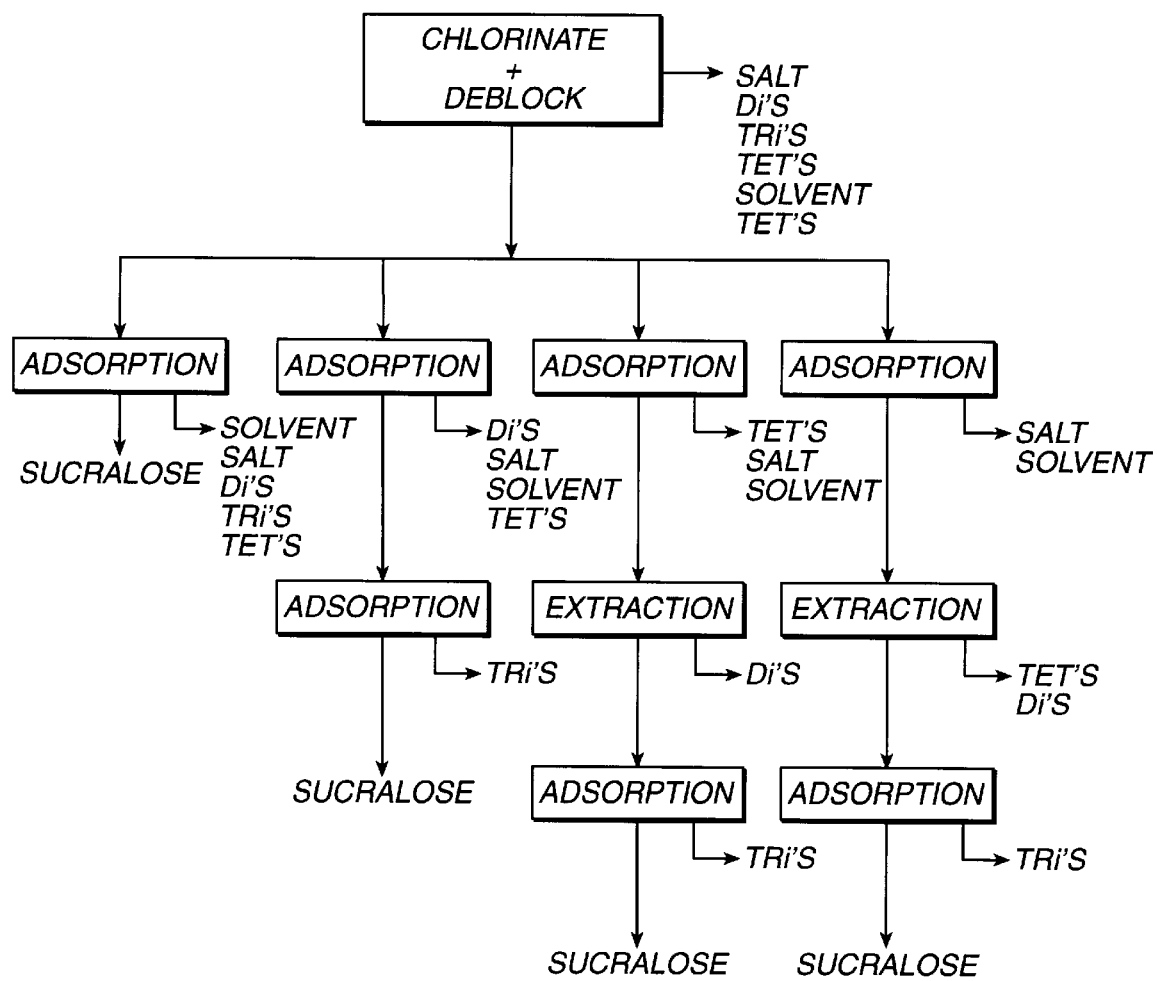

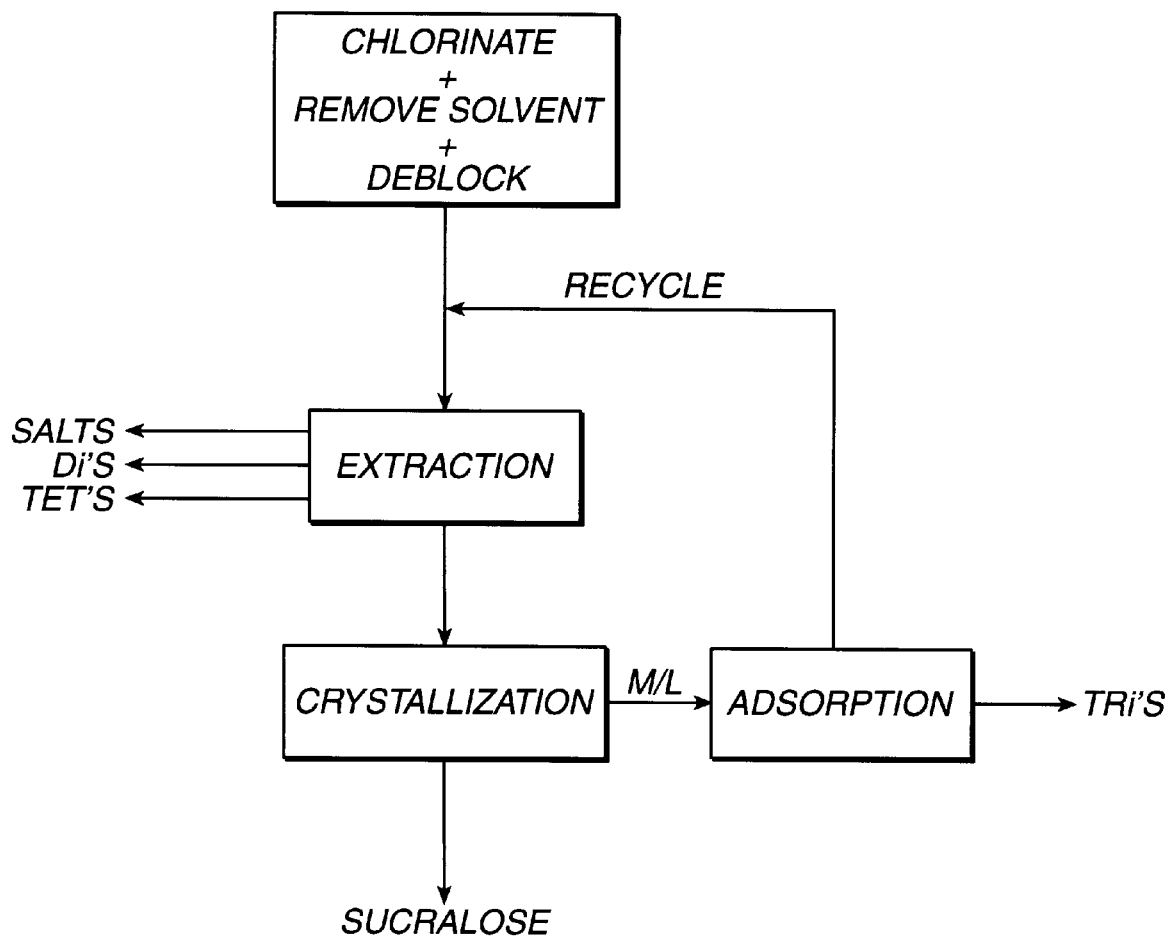
FIG. C
ADSORPTION AS A YIELD-ENHANCING ADJUNCT TO CRYSTALLIZATION.

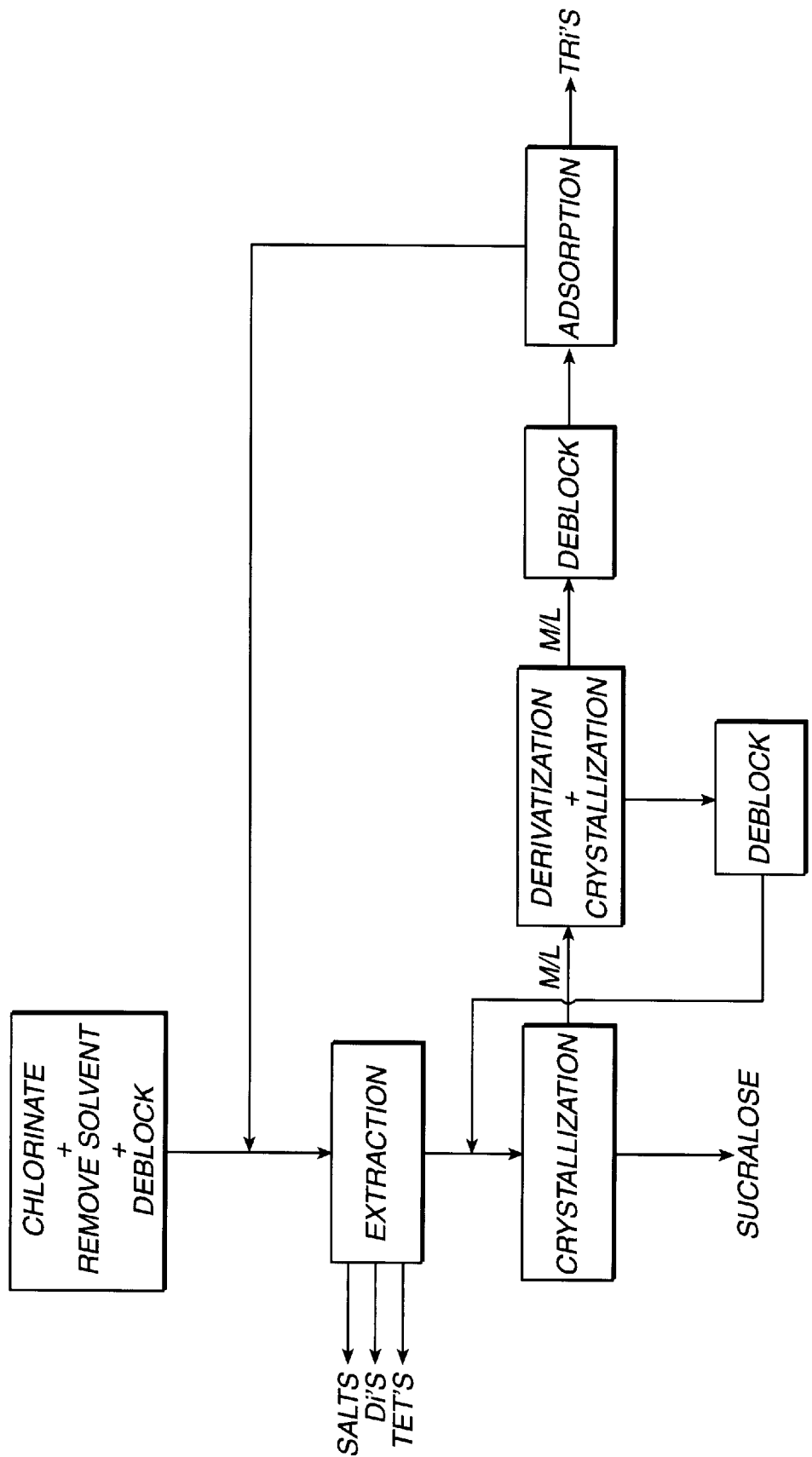

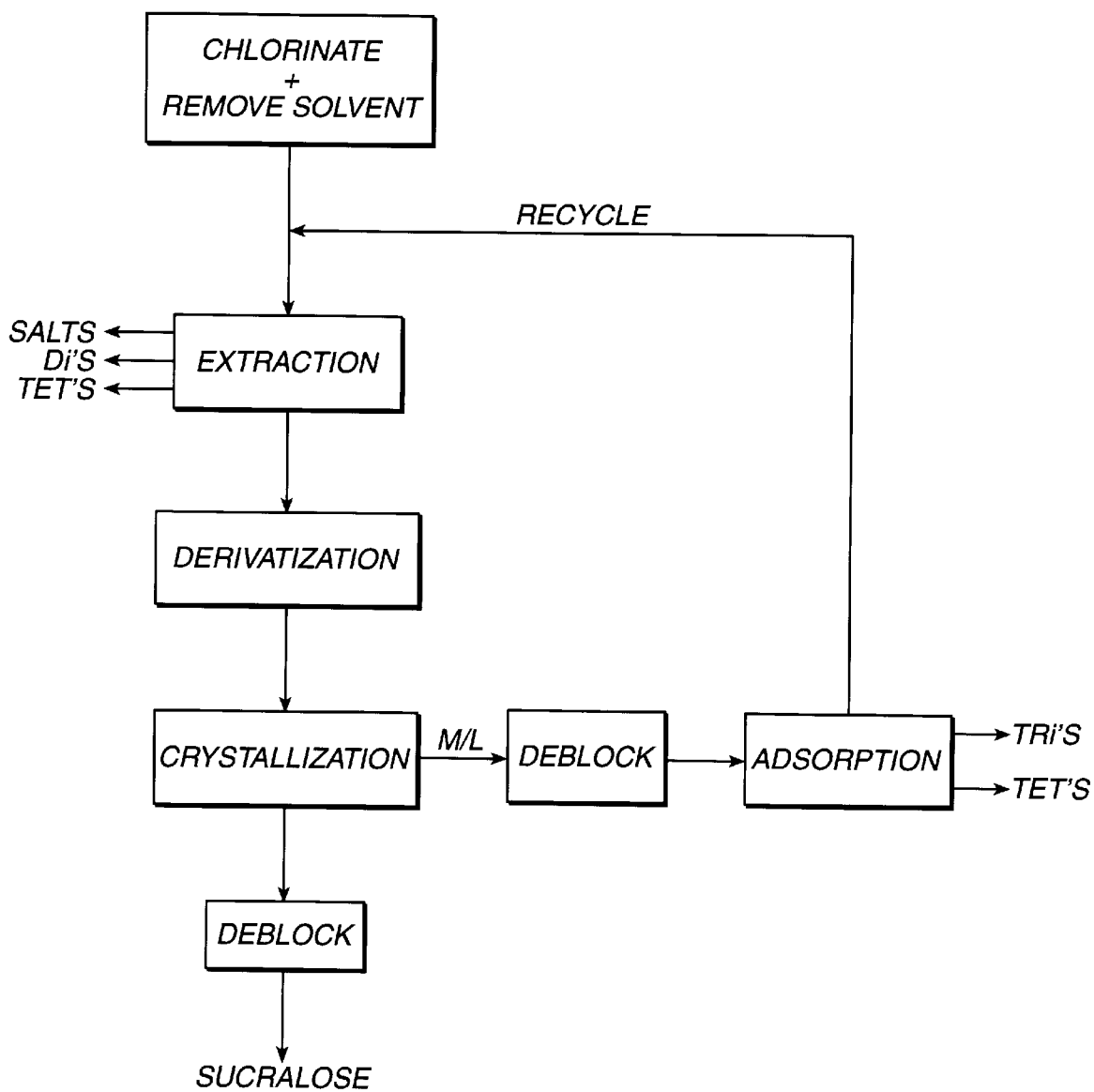
FIG. E
ADSORPTION AS A YIELD-ENHANCING ADJUNCT TO
DERIVATIZATION AND CRYSTALLIZATION

CHROMATOGRAPHIC PURIFICATION OF CHLORINATED SUCROSE

This application claims benefit of Provisional application Ser. No. 60/046,980, filed Feb. 13, 1997.

The invention relates to a process for purifying chlorinated sucrose such as the high intensity sweetener sucralose, by chromatography.

BACKGROUND OF THE INVENTION

Selective modification of sucrose presents a major synthetic challenge because of the multiplicity of reactive OH groups and the acid lability of the glycosidic linkage. When the target of interest is the commercially important non-nutritive sweetener, sucralose, i.e., 4,1', 6'-trichloro-4,1', 6'-trideoxygalactosucrose (in the process of making the compound, the stereo configuration at the 4 position is reversed; therefore, sucralose is a galacto-sucrose), the difficulty is compounded by a need to chlorinate the less reactive 4- and 1'-positions, while leaving intact the more reactive 6-position. In spite of the numerous strategies developed to preblock the 6-position, usually by forming a sucrose-6-acylate such as sucrose-6-acetate and removing the blocking moiety as by hydrolysis after chlorination and so minimize side reactions, the crude chlorination product inevitably still contains some unwanted di-tri- and tetra-chlorinated sucroses (hereinafter, respectively referred to as Di's, Tri's and Tet's), as well as the high-boiling solvent used in the reaction and the chloride salts generated in neutralization after the chlorination step. In aggregate, these present a multi-faceted purification problem and a pivotal concern to the overall economics of sucralose manufacture. The prior art teaches various combinations of distillation liquid-liquid extraction, crystallization and/or derivatization to effect said purification. We have now discovered that adsorption technology exploiting the differing affinities of the associated components for particular solid adsorbents can be applied, in various liquid-solid designs, alone or in combination with the aforementioned processes, to offer significant operational advantages over the prior art.

The simplest form of adsorption technology is the pulse mode, wherein a single concentrated mixture is introduced onto an adsorbent column, and subsequently separated into its various components under passage of a suitable desorbent. Axial or radial flow devices may be used, depending on the pressure drop needs of the system. FIG. 1 depicts a generic separation in this mode of a mixture of components (or bands of components), A, B, and C, where affinity for the adsorbent follows an order, A>B>C, and $t_o$ through $t_n$ denote increasing elution time (or column length). Operationally, the take-off port may be positioned at $t_3$ or later, if all 3 bands need resolving; or at any point along the $t_o$ to $t_3$ continuum, if some degree of overlap is tolerated. In the latter instance, if the focus is solely to purify A and C, without concern for B, one option is to just take the early and late slices of the overlapping profile at $t_2$ and intermix the center-cut with fresh feed; the composite recycling back to the same, or cascading forward to, a second column. In these continuous pulse modes, maximum productivity is sought by operating close to the minimum acceptable resolution and minimizing the interval between feed pulses; in effect minimizing the amount of desorbent used to that which just maintains the leading edge of one pulse from catching up with the trailing edge of the one immediately preceding.

Truly continuous operation, demanding simultaneous flow of feed, desorbent and take-off(s), is also possible. In one approach, termed continuous annular chromatography (CAC), an annular column is slowly rotated about its axis, to cause the feed and desorbent, being injected from the top, to separate into helical bands in the annulus—and be duly withdrawn through discrete ports at the bottom. Though continuous in operation, this design resembles pulse in its less than efficient use of adsorbent. An alternate mechanical arrangement, termed simulated moving bed (SMB), is greatly preferred—minimizing adsorbent and desorbent usage and maximizing take-off concentrations. It consists of a fixed-bed, comprising several serial sections or columns in a closed loop, each individually capable of receiving and relieving liquid flow. In operation, the desorbent, feed and take-off ports, held in a fixed arrangement relative to one another, ratchet forward, at a fixed time interval (referred as the step time), in a direction cocurrent with the liquid flow—thus, simulating counter-current movement of the liquid-adsorbent contact. This design has won wide acceptance in the manufacture of a broad range of commodity chemicals, e.g., xylene, ethylbenzene, high fructose corn syrup and sugar, with commercial units operating up to 22 ft. in diameter. Yet another mode, termed continuous cocurrent SMB, has also been described continuously cascading the overlap fractions through a plurality of columns, utilizing an SMB-type valve-switching arrangement.

It will be understood from the above discussion that in order to apply any or all of these adsorption techniques to a particular service, one first has to discover an adsorbent-desorbent pair capable of effecting the requisite separation, and that the single-pulse mode, stripped of the mechanical complexity of the more continuous approaches, provides the intrinsic picture of the relative separation factors involved. This picture, or chromatogram, records the concentrations of each constituent in individual fractions, collected along a volumetric line, denoting desorbent flow. By convention, where the elution order directly reflects the increasing polarity of the components, the profile is termed "normal phase". This arises when a polar adsorbent is combined with a non-polar desorbent, e.g., cyclohexane on silica-gel. In contrast, the term "reversed phase" describes the pairing of an apolar adsorbent with a polar desorbent—and an elution order of decreasing polarity.

A broad diversity of application is possible—both in regard to the position and composition of the actual stream being treated. In cases, where the adsorption step can be situated in benign aqueous environments, organic resins are permitted. When the environment contains a harsh organic solvent, one is constrained to the more inert adsorbents, e.g., molecular sieves, silica-gel, zeolites, and activated carbon. We have now found that both classes of adsorbent, when combined with appropriate desorbents, can be utilized in systems applicable to a wide range of sucralose purification services.

BRIEF SUMMARY OF THE INVENTION

The invention provides a process for separating, in the liquid phase, a reaction mixture which comprises a first chlorinated sucrose and at least one additional component selected from the group consisting of at least one other chlorinated sucrose different from said first chlorinated sucrose, salt and solvent, by injecting said reaction mixture onto a fixed bed of solid adsorbent and treating with a desorbent such that:

(a) the first chlorinated sucrose passes through the adsorbent into a first recoverable product stream rich in said first chlorinated sucrose at a rate, which is different than the rate at which, (b) at least one of said additional components passes through the adsorbent into at least a second recoverable stream rich in said additional component.

Figure 1:
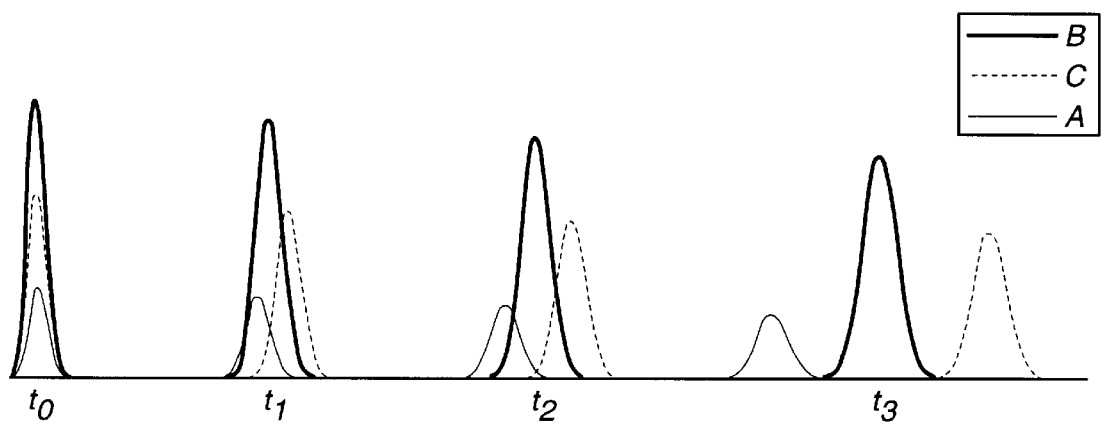
FIG. 1 is an illustrative generic separation of a mixture via adsorption.

FIG. A is a chart showing adsorption technology options following deblocking, with removal of solvent.

FIG. B is a chart showing adsorption technology options following deblocking, with removal of solvent.

FIG. C is a chart showing adsorption as a yield-enhancing adjunct to crystallization.

FIG. D is a chart showing adsorption and derivatization as yield-enhancing adjunct to crystallization.

FIG. E is a chart showing adsorption as a yield-enhancing adjunct to derivatization and crystallization.

DETAILED DESCRIPTION OF THE INVENTION

In a preferred aspect, the process of the invention is employed to purify sucralose. In carrying out the process of the invention for the purification of sucralose, the typical chlorinated sucrose mixture will contain a mixture of chlorinated di-, tri- and tetra-chlorinated sucroses of the formula:

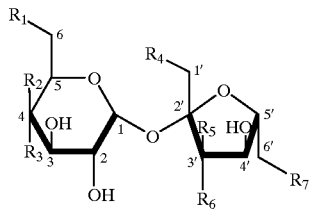

wherein for the various chlorinated sucroses:

4,6'- : $R_2$, $R_7$=Cl; $R_1$, $R_4$, $R_6$=OH ; $R_3$, $R_5$=H

1', 6'- $R_4$, $R_7$=Cl; $R_1$, $R_3$, $R_6$=OH ; $R_2$, R=H 4,1'- : $R_2$, $R_4$=Cl; $R_1$, $R_6$, $R_7$=OH ; $R_3$, $R_5$=H 6,6'- $R_1$, $R_7$=Cl; $R_3$, $R_4$, $R_6$=OH ; $R_2$, $R_5$=H 4,1', 6'- : $R_2$, $R_4$, $R_7$=Cl; $R_1$, $R_6$, =OH ; $R_3$, $R_5$=H 4,1', 6'- $R_3$, $R_4$, $R_7$=Cl; $R_1$, $R_6$=OH ; $R_2$, $R_5$=H 6,1', 6'- : $R_1$, $R_4$,$R_7$=Cl; $R_3$, 4=OH; $R_2$, $R_5$=H 4,6,6'- $R_1$, $R_2$, $R_7$=Cl; $R_4$, $R_6$=OH ; $R_3$, $R_5$=H 6,4,1', 6'-: $R_1$, $R_2$, $R_4$, $R_7$=Cl;=OH ; $R_3$, $R_5$=H 4, 1', 4'46'-: $R_2$, $R_4$, $R_5$, $R_7$=Cl; $R_1$=OH ; $R_3$, $R_6$=H.

By way of illustrative explanation, 4,6'-dichlorosucrose is represented by the formula when $R_2$ and $R_7$=Cl; $R_1$, $R_4$ and $R_6$=OH; and $R_3$ and $R_5$=H. The second entry for the 4,1'6 chlorinated sucrose derives from an inversion of substituents on carbon number 4, resulting in 4, 1', 6'-trichlorosucrose, the sixth listed compound, formally an epimer of sucralose, ie., 4,1', 6'-trichloro-galactosucrose, the fifth listed compound.

The invention employs a reaction mixture which comprises a first chlorinated sucrose and at least one additional component selected from the group consisting of at least one other chlorinated sucrose different from said first chlorinated sucrose, salt and solvent. When being employed to purify sucralose, the reaction mixture used in the invention can be the neutralized reaction product of the sucrose-6-ester chlorination disclosed in Walkup et al., U.S. Pat. No. 4,980,463, the disclosure of which is incorporated herein by reference. In that case, the reaction mixture will contain sucralose-6-ester (such as sucralose-6-acetate or sucralose-6-benzoate), probably at least one other chlorinated sucrose (including esters thereof); the tertiary amide solvent for the chlorination reaction (preferably N,N-dimethylformamide); various salt by-products of the chlorination and neutralization reaction (including alkali, alkali earth metal, ammonium and alkyl ammonium chlorides, for example, sodium chloride and dimethylamine hydrochloride, as well as alkali metal formats such as sodium formate); and water. Sucralose-6-ester is represented by the formula shown above wherein $R_2$, $R_4$, and $R_7$=Cl; $R_1$=an acyloxy group such as acetoxy or benzoyloxy; $R_6$=OH, and $R_3$ and $R_5$=H. The reaction mixture in this case may contain other chlorinated sucroses that are also esterified in the 6-position.

Alternatively, the chlorination reaction mixture (produced by the process of Walkup et al.) can be subjected to steam stripping or the like to remove the tertiary amide solvent (as is disclosed in Navia et al., U.S. Pat. No. 5,530,106, the disclosure of which is incorporated herein by reference), followed by hydrolysis to remove the 6-acyl moiety, to produce another reaction mixture that can be used in the purification process of the invention. In this case, the reaction mixture used in the process of this invention will contain sucralose; probably other chlorinated sucroses; various salt by-products of the chlorination and neutralization reaction (including alkali, alkali earth metal, ammonium and alkyl ammonium chlorides, for example, sodium chloride and dimethylamine hydrochloride, as well as alkali metal formates such as sodium formate); water; probably a small amount (less than 1 or 2%, by weight, of the reaction mixture) of the tertiary amide solvent; and possibly some remaining sucrose-6-ester compounds (in the case where the hydrolysis to remove the 6-acyl moiety was not complete).

Another reaction mixture that can be used in the process of the invention can be produced from the steam stripped and hydrolyzed product of the process disclosed by Navia et al. by recrystallization (as is also disclosed in Navia et al.) to remove salts and some of the other (i.e., non-sucralose) chlorinated sucroses, mostly di's. In this case, the reaction mixture used in the invention will contain sucralose and other chlorinated sucroses (mostly tril's and tetra's); an organic solvent, such as ethyl acetate; and a small amount of water.

FIG. A diagrams a set of schemes, particular to a situation, wherein first the high boiling chlorination solvent, typically an amide such as N,N-dimethylformamide, is removed and the crude chlorination product deblocked (as by alkaline hydrolysis to remove the acyl group from, e.g., sucralose-6-acetate). The emerging aqueous stream can be purified of its unwanted salts, Di's, Tri's and Tet's in any of four broad ways; three of which involve variously splitting the purification load between extraction and adsorption - the order of which being non-critical. The fourth example, deploying adsorption alone, will be recognized as the primary embodiment for purposes of demonstration of this invention, involving as it does the widest scope of constituents to be separated; the adsorption loads in each of the other three examples being but subsets thereof.

Figure 2:
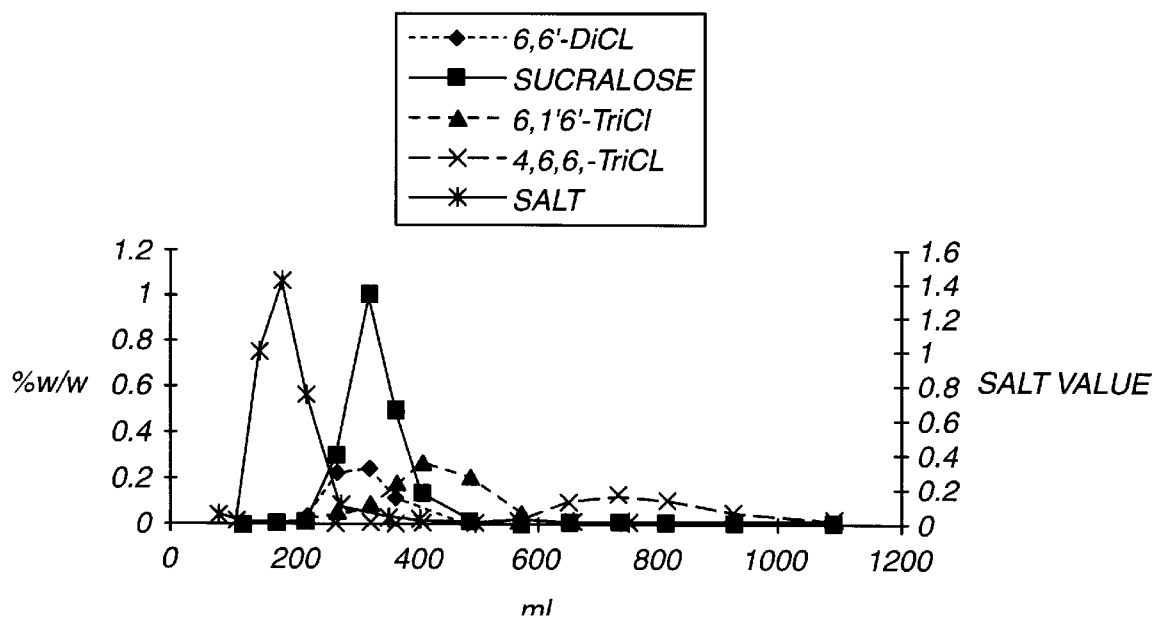
FIG. 2 is a chromatogram with sodium sulfonic acid resin, 4% DVB, as adsorbent and water as desorbent.
Figure 3:
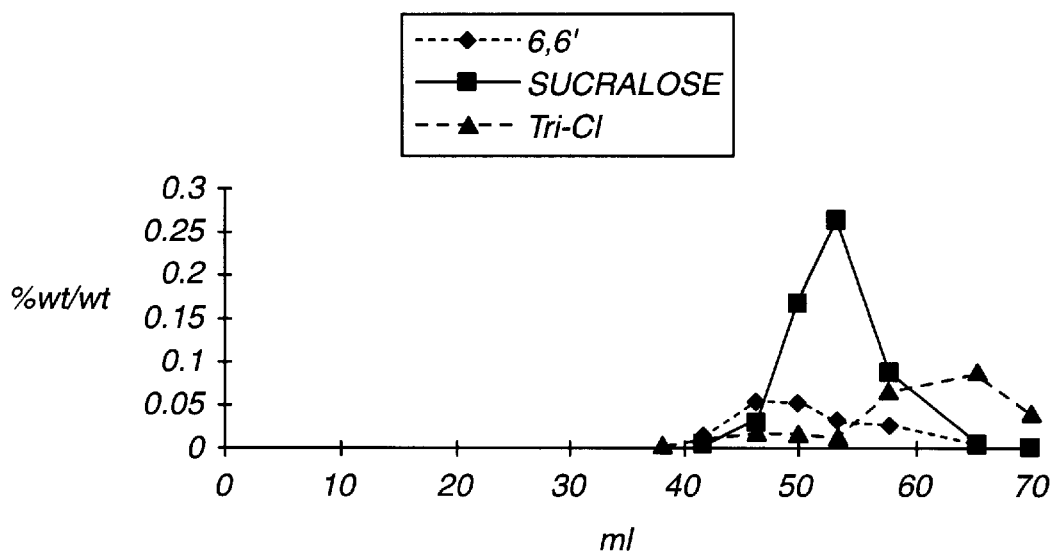
FIG. 3 is a chromatogram with sodium sulfonic acid resin, 2% DVB, as adsorbent and water as desorbent.
Figure 4:
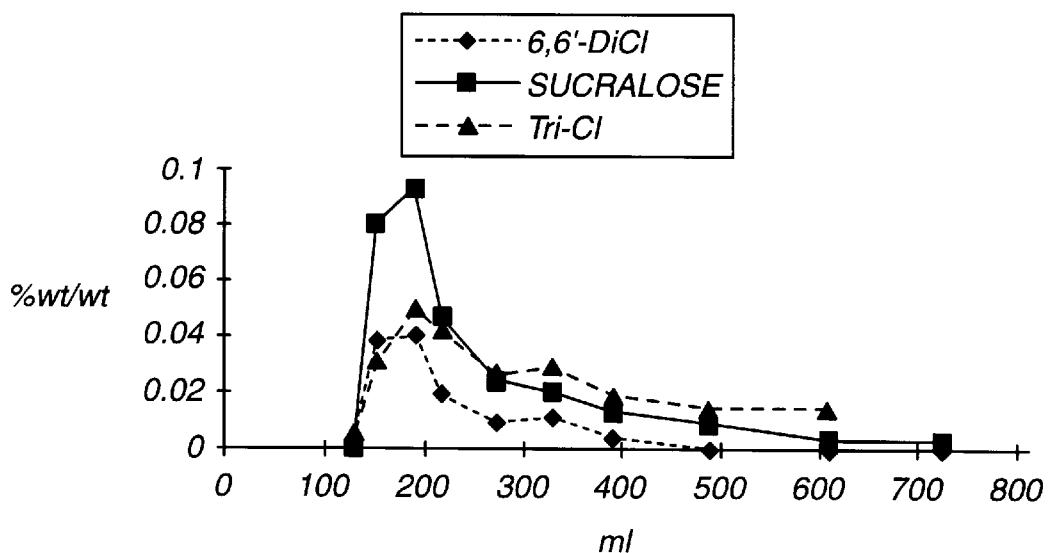
FIG. 4 s a chromatogram with sodium sulfonic acid resin, 6% DVB, as adsorbent and water as desorbent.

FIG. 2 presents the results obtained with a reversed phase system, employing a polystyrene-based sodium sulfonic resin, crosslinked with 4% divinylbenzene, as adsorbent, and straight water as desorbent. An elution order: salt >Di's >6,6'>sucralose >6,1', 6,>4,6,6'>Tet's is thus revealed. We have discovered the degree of crosslinking and its resulting influence on levels of difusion, to be important in the use of these organic resin adsorbents: 2% (FIG. 3) and 4% (FIG. 2) divinylbenzene affording good separations, 6% (FIG. 4) and above showing little or no discrimination. Further, we have discovered the efficiency of separation to be invariant to the choice of cation—with no significant difference being found between alkali or alkaline earth metals. This stands in marked contrast to other carbohydrate systems that are more sensitive to selectivity or stability considerations. Thus, the divalent alkaline earth metals are favored in the prior art: (a) in the case of fructose/glucose, where the degree of separation largely derives from the relative ease with which these monosacchrides can orient their hydroxyl groups to coordinately replace the water molecules held in the cationic hydration sphere, and (b) in the case of oligosaccharides, where the alkali metals afford radical hydrolytic destruction of substrates. A further point of distinction from the prior art relates to the mode of interaction observed. Unlike the resin interactions of (a) glucose/fructose,(b) sucrose/raffinose and oligosaccharides, which all show an elution order of increasing molecular size, reflecting the relative rates of penetration/diffusion through the beads the elution profile of the chlorinated sucroses suggests rather the increasing hydrophobicity of the components to be the determining factor—more indicative of van der Waals-type interactions on the surface. Thus, the larger entities our systems, i.e., the Tet's, rather than eluting early in line with the size exclusion behavior of the prior art, elute late because of their highly hydrophobic nature—and vice versa, the Di's, elute early, because of their more hydrophilic nature, rather than late, as would be expected from their smaller size.

Figure 5:
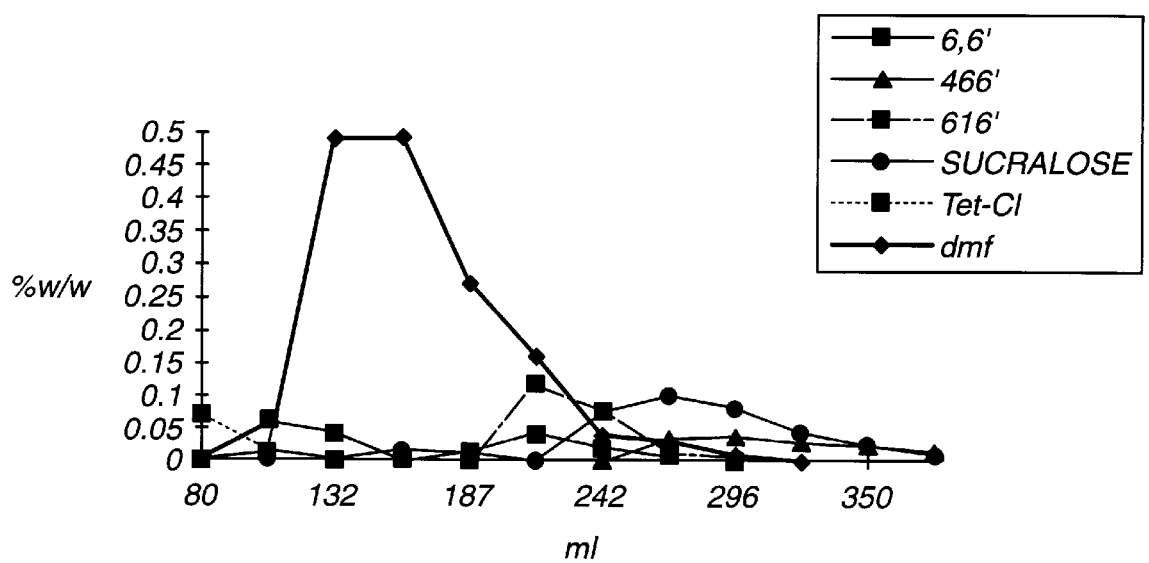
FIG. 5 is a chromatogram with silica-gel as adsorbent and ethyl acetate (2% water) as desorbent.

FIG. B depicts a further set of embodiments that build on those of FIG. A and extend the scope of adsorption utility back further in the sucralose manufacturing process, to a position prior to removal of the chlorination solvent. Again, the branch deploying adsorption alone constitutes the primary embodiment; those involving assistance from extraction and/or a second turn of adsorption being subsidiary. Here, as shown in FIG. 5, a combination of silica-gel as adsorbent and ethyl acetate as desorbent has revealed a novel approach to separating the high boiling chlorination solvent. The weakly retained amide runs ahead of the carbohydrates close to the desorbent front; where upon take-off it is fractionally distilled—the ethyl acetate being recycled as desorbent and the amide being flashed free of its solutes. This provides a less energy-intensive alternate to the steam stripping, taught in the prior art (Navia et. al., cited above).

Figure 6:
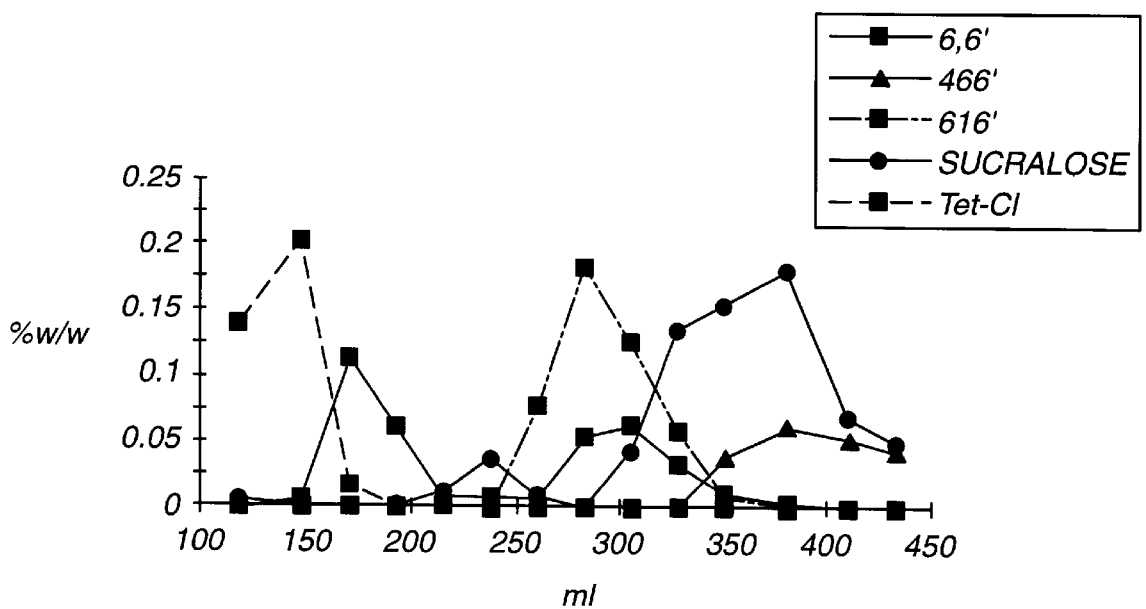
FIG. 6 is a chromatogram with silica-gel as adsorbent and ethyl acetate (2% water) as desorbent.
Figure 7:
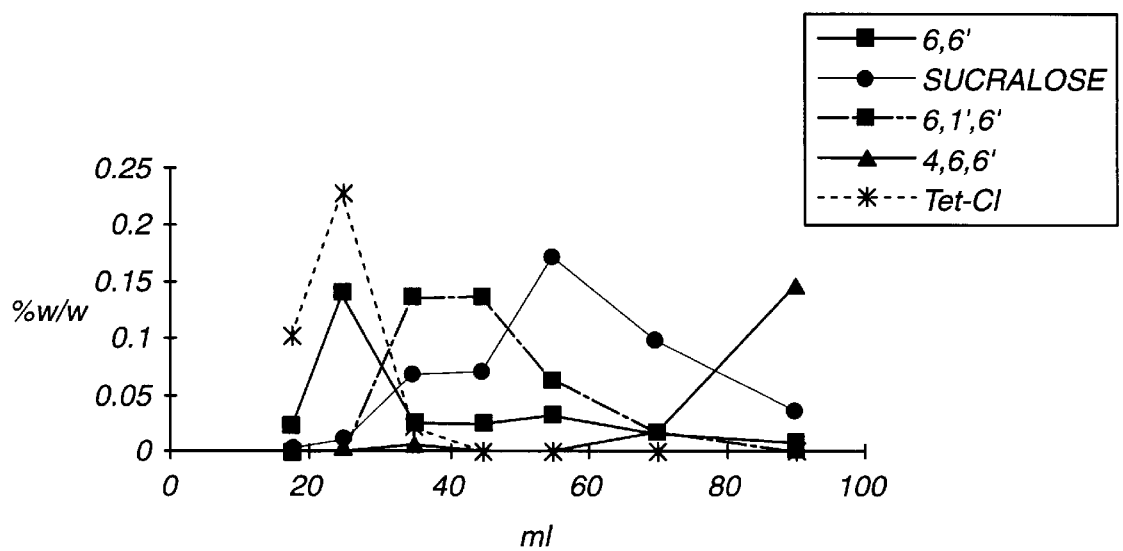
FIG. 7 is a chromatogram with silica-gel as adsorbent and ethyl acetate (5% methanol) as desorbent.

Moreover, as we open up the chromatographic window on this system, (FIGS. 5–7) to also include separating the carbohydratesone from another with an elution order : Tet's>6,6'>DMF>6,1', 6'>sucralose>4,6,6'>Di's—a wider utility emerges, whereby we may configure a variety of adsorption-based purification processes. One general approach is to first purge the chromatographic extremes, either by adsorption alone (e.g, via successive binary separations) or by a combination of adsorption and liquid-liquid extraction. Underpinning these liquid-liquid extracations is the wide disparity in hydrophilicity seen between the three broad homologous classes, following an order: Di's>Tri's>Tet's—in line with the diminishing number of hydroxyl groups that remain on successive substitution with chlorine. In the resulting setting of the isomeric center cut, however, such hydrohilicity differences between constituents (6,6'->sucralose>6,1', 6'-, 4,6,6,'-) shrink, to where the number of equilibrium stages required (for liquid-liquid extraction) becomes commercially prohibitive. In this key service, we have discovered that adsorption differentiates itself, quite markedly, from all other process technologies—in terms of yield and operational performance. The asymmetric elution order (sucralose>6,1', 6'->4,6,6'-) found with the reversed phase system (FIG. 2) proves particularly positive, in that it allows coincident removal of the 4,6'6'- and 6,1-,6'—impurities via a single binary split on an SMB arrangement—carrying (as described earlier) all the inherent efficiencies of continuous operation and maximum utilization of adsorbent and desorbent. The normal phase approach (FIGS. 5–7), displaying a symmetric elution order (6,1', 6'->sucralose >4,6,6'-) is also an option, albeit demanding two such binary SMB separations or a single variant capable of multiple take-offs.

Figure 8:
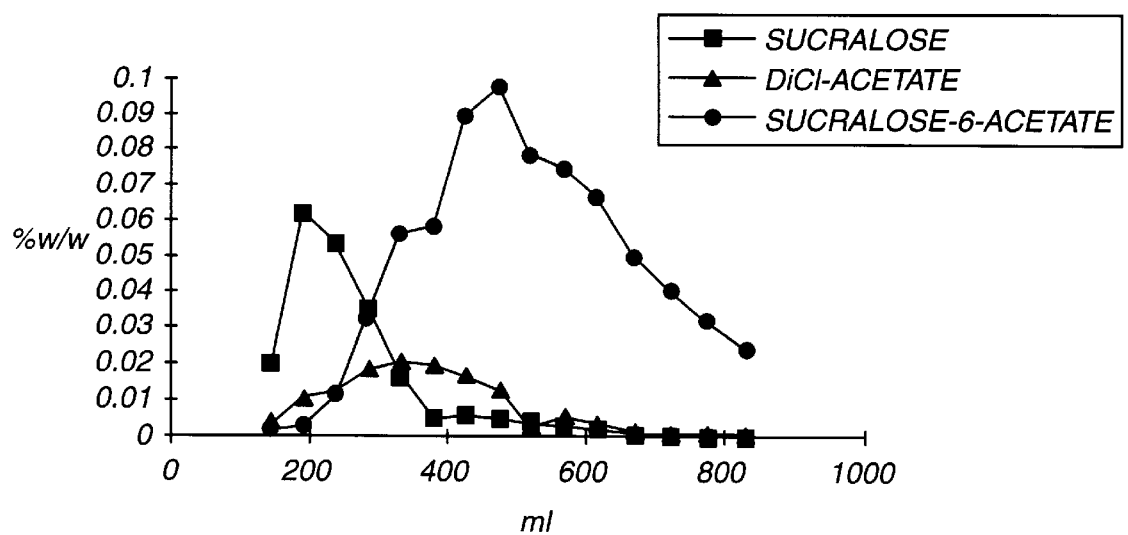
FIG. 8 is a chromatogram with sodium sulfonic acid resin, 4% DVB, as adsorbent and water as desorbent.

In either case, it will be recognized that the sucralose isomeric separation discovered is unrivaled in the prior art. Crystallization, the only other direct contender, widely deployed, results in finite yields, self-limited by the "poisoning" activity of the unwanted isomers that build in the mother liquor—even when 2nd crop strategies are included. This resulting mother liquor, containing sizable quantities of sucralose, can only be directly resolved via adsorption, as above (FIG. C). Derivatization of the isomeric center cut is, of course, also feasible, albeit with the extra operational complexity and reagent use, associated with the addition of two new chemical steps—i.e. blocking and deblocking (FIG. D and E). Moreover, the derivatized intermediate, typically a perester is purified by crystallization wherein mother liquor losses still obtain—similar to, albeit less than, those encountered with the un-derivatized sucralose. We offer further illustrative embodiments in FIGS. C–E, deploying our adsorption technology as yield-enhancing adjuncts to these crystallization and/or derivatization approaches. Finally, the opportunities for designing even more radical purification processes, by applying adsorption technology to esterified reaction mixtures prior to hydrolysis, such as those found, for instance, in the earlier referenced processes of Walkup et al., U.S. Pat. No. 4,980,463 and Navia et al., U.S. Pat. No. 5,530,106, are also shown to be possible. In particular, the reverse-phase chromatographic picture, as detailed in FIG. 8. showing an elution order, sucralose >DiCl-monoacetates >sucralose-6-acetate, can be multifariously exploited to purify, the sucralose-6-aetate, so that subsequent deacetylation yields pure sucralose directly.

What is claimed is:

1. A process for the liquid phase separation of a chlorinated sucrose reaction mixture, wherein said mixture is comprised of a first chlorinated sucrose and at least one additional component selected from the group consisting of at least one other chlorinated sucrose different from said first chlorinated sucrose, salt and solvent, by injecting said reaction mixture onto a fixed bed of solid absorbent and treating with a desorbent such that:

(a) the first chlorinated sucrose passes through the absorbent into a first recoverable product stream rich in said first chlorinated sucrose at a rate which is different than the rate at which, (b) the additional components pass though said absorbent into at least one additional stream rich in said additional components.

2. The process of claim 1, wherein the reaction mixture includes at least two chlorinated sucroses selected from the group consisting of dichlorinated sucroses, trichlorinated sucroses and tetrachlorinated sucroses of the formula:

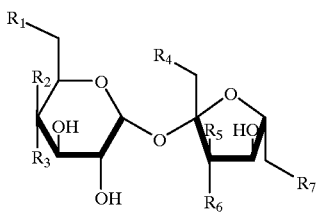

wherein for the various chlorinated sucroses:

4,6'- : $R_2$, $R_7$=Cl; $R_1$, $R_4$, $R_6$=OH ; $R_3$, $R_5$=H
1', 6'- $R_4$, $R_7$=Cl; $R_1$, $R_3$, $R_6$=OH ; $R_2$, R=H
4,1'- : $R_2$, $R_4$=Cl; $R_1$, $R_6$, $R_7$=OH ; $R_3$, $R_5$=H
6,6'- $R_1$, $R_7$=Cl; $R_3$, $R_4$, $R_6$=OH ; $R_2$, $R_5$=H
4,1', 6'- : $R_2$, $R_4$, $R_7$=Cl; $R_1$, $R_6$, =OH ; $R_3$, $R_5$=H
4,1', 6'- $R_3$, $R_4$, $R_7$=Cl; $R_1$, $R_6$=OH ; $R_2$, $R_5$=H
6,1', 6'- : $R_1$, $R_4$,$R_7$=Cl; $R_3$, 4=OH; $R_2$, $R_5$=H
4,6,6'- $R_1$, $R_2$, $R_7$=Cl; $R_4$, $R_6$=OH ; $R_3$, $R_5$=H
6,4,1', 6'-: $R_1$, $R_2$, $R_4$, $R_7$=Cl;=OH ; $R_3$, $R_5$=H
4,1', 4'46'-: $R_2$, $R_4$, $R_5$, $R_7$=Cl; $R_1$=OH ; $R_3$, $R_6$=H.

3. The process of claim 1, wherein the reaction mixture is an actual process stream used in the manufacture of sucralose.

4. The process of claims 1, 2, or 3 wherein the salt includes a salt selected from the group consisting of alkali, alkali earth metal, ammonium and alkyl ammonium chlorides.

5. The process of claims 1, 2, or 3 wherein the solvent is a tertiary amide.

6. The process of claim 5 wherein the tertiary amide is N,N-dimethylformamide.

7. The process of claims 1, 2, and 3 wherein the fixed bed solid adsorbent is silica-gel and the desorbent is an organic solvent.

8. The process of claims 1, 2 or 3 wherein the fixed bed solid adsorbent is a porous gel cation-exchange resin and the desorbenet is water.

9. The process of claims 1, 2 or 3 wherein the chromatographic separation is carried out in pulse, continuous-pulse, or continuous, mode.

10. The process of claims 1, 2 or 3 wherein the fixed bed adsorbent is contained within a column, the feed and desorbent being injected at one end and the separated or enriched fractions, following an axial traverse, being collected at the other.

11. The process of claims 1, 2 or 3 wherein the fixed bed adsorbent is contained within a column, the feed and desorbent being injected at the circumference and the separated or enriched fractions, following a radial traverse, being collected through an inner channel at the center.

12. The process of claims 1, 2 or 3 wherein the fixed bed adsorbent is contained within a column, the feed and desorbent being injected through an inner channel at the center and the separated or enriched fractions, following a radial traverse, being collected at the circumference.

13. The process of claims 1, 2, or 3 wherein the fixed bed of solid adsorbent is contained within a vertically mounted, rotating annulus, the feed and desorbenet being injected at the top and the separated or enriched fractions being collected at the bottom.

14. The process of claims 1, 2 or 3 wherein the fixed bed of solid adsorbent is contained within several serial sections or columns in a closed loop, each individually capable of receiving and relieving fluid, and equipped with a fixed arrangement of feed, desorbent and take-off ports, that ratchet forward at fixed intervals in a direction cocurrent with the liquid flow, simulating countercurrent movement of the fixed-bed adsorbent.

15. The process of claims 1 or 3 wherein said first chlorinated sucrose is represented by the formula:

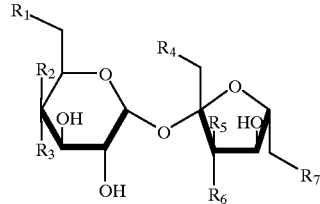

wherein $R_2$, $R_4$, and $R_7$=Cl; $R_1$=an acyloxy group; $R_6$=OH; and $R_3$ and $R_5$=H.

16. The process of claim 15 wherein the acyloxy group is an acetoxy group.

17. The process of claim 15 wherein the acyloxy group is a benzoyloxy group.

* * * * *